US012539029B2

(12) United States Patent
Raymondos

(10) Patent No.: US 12,539,029 B2
(45) Date of Patent: Feb. 3, 2026

(54) INTUBATION DEVICE

(71) Applicant: Konstantinos Raymondos, Hannover (DE)

(72) Inventor: Konstantinos Raymondos, Hannover (DE)

( * ) Notice: Subject to any disclaimer, the term of this patent is extended or adjusted under 35 U.S.C. 154(b) by 121 days.

(21) Appl. No.: 18/407,714

(22) Filed: Jan. 9, 2024

(65) Prior Publication Data

US 2024/0268654 A1 Aug. 15, 2024

(30) Foreign Application Priority Data

Nov. 18, 2022 (EP) .................................... 22075014

(51) Int. Cl.
*A61B 1/267* (2006.01)
*A61B 1/32* (2006.01)

(52) U.S. Cl.
CPC .............. *A61B 1/2673* (2013.01); *A61B 1/32* (2013.01)

(58) Field of Classification Search
CPC ........... A61B 1/267; A61B 1/008; A61B 1/32; A61M 16/00; A61M 16/0418
See application file for complete search history.

(56) References Cited

U.S. PATENT DOCUMENTS 5,938,591 A * 8/1999 Minson .................. A61B 1/267 600/199
7,153,260 B1 * 12/2006 Girgis .................... A61B 1/267 600/199
7,695,433 B2 * 4/2010 Simons .................. A61B 1/267 600/203
8,715,172 B1 * 5/2014 Girgis ...................... A61B 1/05 600/188
2006/0247496 A1 11/2006 Tjong
2007/0213594 A1 * 9/2007 Nguyen ................. A61B 1/267 600/190
2008/0167530 A1 * 7/2008 Minson .................. A61B 1/267 600/194

(Continued)

FOREIGN PATENT DOCUMENTS

CN 114176497 A * 3/2022 ............... A61B 1/32
EP 2535075 A1 * 12/2012 ......... A61B 1/00181

*Primary Examiner* — Ellen C Hammond
(74) *Attorney, Agent, or Firm* — WCF IP

(57) ABSTRACT

The invention relates to an intubation device for intubating a patient with an endotracheal tube, having the following features:

a) a handle for holding the intubation device,
b) a rigid guide rail which is connected to the handle and which has a guide channel, extending in a longitudinal direction from a patient-remote end to a patient-near end of the guide rail, for guiding the endotracheal tube, and has an upper face facing toward the patient's tongue during the intubation procedure,
c) an epiglottis lifter for lifting the patient's epiglottis, wherein the epiglottis lifter is mounted movably on a component of the intubation device via at least one bearing element,
d) at least one optical detection device in the patient-near region on the guide rail and/or at least one optical detection device in the patient-near region on the epiglottis lifter,
e) wherein the epiglottis lifter, at least in the patient-near region, in particular in a bend region of the guide rail, covers and largely or completely closes the guide rail or at least the guide channel on the upper face of the guide rail.

14 Claims, 8 Drawing Sheets

(56) References Cited

U.S. PATENT DOCUMENTS

| | | | | |
|---|---|---|---|---|
| 2016/0095509 | A1* | 4/2016 | Nacouzi ............. | A61B 1/00105 600/193 |
| 2017/0181614 | A1* | 6/2017 | Bartozzi .............. | A61B 1/2673 |
| 2017/0224200 | A1 | 8/2017 | Uesugi et al. | |
| 2019/0175008 | A1* | 6/2019 | Nagele ............... | A61B 1/00183 |
| 2020/0015832 | A1 | 1/2020 | Levine et al. | |

* cited by examiner

INTUBATION DEVICE

The invention relates to an intubation device for intubating a patient with an endotracheal tube. Generally, the invention relates to the field of laryngoscopy.

State of the Art in Laryngoscopy and Various Techniques for Opening the Upper Airways In principle, it is possible to distinguish between four different laryngoscopy techniques or techniques for opening the upper airways:

1. Endoscopic laryngoscopy with a flexible or rigid endoscope.
2. Standard laryngoscopy with a blade or mouth gag.
3. Exclusive opening of the deep pharyngeal region and lifting of the epiglottis.
4. Opening of the airways with what is called an “oropharyngeal airway”

What is common to all techniques is that the deep pharyngeal region in front of the larynx is opened, and the epiglottis is lifted in such a way that the laryngeal inlet is exposed. In endoscopic laryngoscopy, this is done spontaneously by the patient. In the other techniques, the deep pharyngeal region is actively opened with an aid in such a way that the epiglottis is also lifted. The two methods mentioned under 2. and 3. differ in that, with standard laryngoscopy, pressure must also be applied to the upper parts of the pharynx, the soft-tissue parts of the throat and the root of the tongue, and the mouth has to be additionally opened.

In endoscopic laryngoscopy, a flexible or rigid endoscope is inserted in such a way that the laryngeal inlet can be viewed. Since this is in most cases done with the patient awake or sedated, the airways in the deep pharyngeal region are usually open. It is therefore usually not necessary to open the airways using an auxiliary device.

The endoscope optics are not protected by a blade or in any other way, and there is no other device for keeping the airway mucosa or airway secretions at a safe distance from the optics. In cases where sedation is too deep, or after induction of anesthesia or in a coma, the airways collapse and the airway mucosa and/or secretions block the view. In clinical routine, an attempt is then made to flush the optics clear.

In order to guide a flexible optical unit around the tongue and epiglottis, so-called “oropharyngeal airways” are also used. However, in patients under anesthesia or in a coma, the opening and in particular the lifting of the epiglottis are often insufficient to allow safe and quick orientation.

When inserting straight, rigid endoscopes, it is also attempted to keep the upper airways open using a thumb. As a rule, however, a standard laryngoscope would then be used to push the tongue upward and then also indirectly lift the epiglottis. The rigid endoscope can also be inserted via a mouth gag or a so-called “rigid tube”: The rigid tube is the simplest form of an endoscope: In this method, with the head of the usually anesthetized patient hyperextended, a tube is inserted in such a way that the laryngeal inlet can be seen directly as in standard laryngoscopy, even without optics. Accordingly, as in standard laryngoscopy, the upper parts of the pharynx, the soft-tissue parts of the throat and the root of the tongue also have to be displaced.

Standard laryngoscopy does not only entail opening the deep pharyngeal region and lifting the epiglottis: In order to allow opening deep down and to be able to effectively transfer the necessary blade pressure to the tissue in the deep pharyngeal region, the pressure also has to be applied to the upper pharyngeal region and to the tongue. In conventional, direct laryngoscopy, pressure is thus also exerted on the upper pharyngeal region, on the tongue and, via the soft-tissue parts of the throat, on the lower jaw, and the mouth has to be opened further. This is done in an attempt to see the laryngeal inlet directly. It may be necessary to hyperextend the head.

In ENT, laryngoscopy is performed with the aid of a mouth gag according to the same principle as in standard laryngoscopy. Under anesthesia, with the head hyperextended, the blade is fixed in order to keep the airways open, and the mouth is also kept open in various stages via an arch fixed to the upper jaw (e.g. Davis-Boyle mouth gag).

When exclusively opening the deep pharyngeal region and lifting the epiglottis, only the deep pharyngeal region is opened, such that the epiglottis is lifted and the laryngeal inlet is exposed. In contrast to the standard procedures mentioned above, much less pressure, if any, is exerted on the upper parts of the pharynx and the tongue, and the mouth does not have to be opened additionally. An example is given in EP 1 439 776 B1. The intubation device described there is inserted into the mouth and positioned deep in the throat without visual monitoring. The guide rail is then pushed forward and/or down. The bracket enclosing the rail remains fixed in the handle. By the resulting separation of guide rail and bracket, the deep pharyngeal space is opened. With the device correctly positioned, the opening of the deep pharyngeal space also lifts the epiglottis, thus exposing the laryngeal inlet. Intubation can then take place, but without guidance by visual monitoring.

Opening of the airways with a so-called “oropharyngeal airway”: In 1908, an oropharyngeal airway was first described, and a soft rubber model was introduced by Güdel in 1933. The standard oropharyngeal airway is still referred to as a “Guedel tube”. In unconscious or sedated patients, an oropharyngeal airway is inserted in order to keep the upper airways open while maintaining spontaneous breathing. It is also inserted after anesthesia is initiated, in order to facilitate mask ventilation. A flange at the upper end of a J-shaped tube is intended to prevent accidental swallowing. Guedel tubes are available in many sizes and are often used in emergencies by medical personnel even without a medical order.

There are many variations, some of which were developed for intubation without visual monitoring. They were later used for endoscopic examination of the airways and also for intubation with visual monitoring using an endoscope.

Problems and Disadvantages in Endoscopic Laryngoscopy

Endoscopic laryngoscopy with rigid or flexible optical units in the unsecured airway can usually only be performed if the airways are kept open by a patient who is conscious or not too deeply sedated. Here, the field of view afforded by standard endoscopes is much smaller than that in standard laryngoscopy, a fact that can make orientation very difficult, especially for beginners.

In cases where sedation is too deep, or under anesthesia or in a coma, the upper airways collapse. It can then become very difficult or even impossible to find one’s way between the mucous membranes adhering to each other. In addition, it is much more likely that the exposed and therefore unprotected optical unit between the mucous membranes will become contaminated with secretions, and therefore the optical unit has to be flushed in order to clear it. If flushing is not effective, the view is nonetheless blocked, and it becomes impossible to distinguish between contamination caused by secretions and the view being blocked by mucous membranes lying on the optical unit. If the mucous membranes lie directly on the unprotected optical unit in the collapsed airways, no view and thus no orientation can be achieved even with effective flushing. In the case of collapsed airways, various airway maneuvers can be attempted in order to open the upper airways. This includes lifting of the lower jaw and/or hyperextension of the head. It is also possible to try pushing the tongue up with the thumb.

Problems and Disadvantages with Other Techniques

In order to open the deep pharyngeal region and lift the epiglottis, it is necessary in standard laryngoscopy, as has been described above, to exert pressure additionally on the upper pharyngeal region and also almost the entire tongue. In this case, the mouth generally also has to be opened further, and the lower jaw has to be raised by pressure over the tongue and the soft-tissue parts of the throat and then also held in this position by hand during the intubation.

Sometimes a great deal of force is needed in order to exert this necessary and very high pressure on the upper pharyngeal region, on the tongue and also, via the soft-tissue parts of the throat, on the lower jaw. The force has to be further increased if, during a difficult laryngoscopy procedure, the head for example cannot be hyperextended, and/or, for example soft-tissue parts hardened by pathological processes or other anatomically altered upper airway structures cannot be lifted and displaced sufficiently. It can then be very difficult or even impossible to obtain a direct view with conventional laryngoscopy or with the rigid tube, or to move the optical unit of a video laryngoscope or endoscope to the desired position. Therefore, securing the airways by means of intubation is made very difficult or impossible.

Even normal and trouble-free standard laryngoscopy is a highly invasive procedure. Dental damage is therefore one of the most common complications of general anesthesia. Due to the great force that is applied, very pronounced defence reflexes are always triggered, with corresponding stress reactions. This has far-reaching consequences for any anesthetization in which intubation is carried out in this way and in which an attempt has to be made to avoid these stress reactions by means of anesthetic agents. However, these anesthetic agents sometimes have significant side effects that can be life-threatening in older patients and especially in patients with certain pre-existing diseases.

Intubation can sometimes even be made difficult because the persons performing the intubation, even on a patient with normal airways, are simply unable to apply the required force. In order not to have to apply this force during ENT procedures on the larynx and also to have one hand free, a mouth gag is used for the laryngoscopy: The required force is applied by means of leverage via a support on the chest and by additional fixing on the upper jaw. Because of the strain resulting from this force, interventions performed with mouth gags must always be performed under anesthesia.

The problem addressed by the invention is to make available an intubation device which can be universally used and which permits rapid and safe intubation, which is gentle on the patients, even under anesthesia.

This problem is solved by an intubation device for intubating a patient with an endotracheal tube, having the following features:

a) a handle for holding the intubation device, in particular for holding it with the whole hand,
b) a guide rail which is connected to the handle and which has a guide channel, extending in a longitudinal direction from a patient-remote end to a patient-near end of the guide rail, for guiding the endotracheal tube, and has an upper face facing toward the patient's tongue during the intubation procedure,
c) an epiglottis lifter for lifting the patient's epiglottis, wherein the epiglottis lifter is mounted movably on a component of the intubation device via at least one bearing element,
d) at least one optical detection device in the patient-near region on the guide rail and/or at least one optical detection device in the patient-near region on the epiglottis lifter,
e) wherein the epiglottis lifter, at least in the patient-near region, in particular in a bend section of the guide rail, covers and largely or completely closes the guide rail or at least the guide channel on the upper face of the guide rail.

Thus, in the region in which it covers the guide rail or at least the guide channel on the upper face of the guide rail, the epiglottis lifter is largely or completely closed and thereby forms a roof over the at least one optical detection device in the patient-near region on the guide rail and/or the at least one optical detection device in the patient-near region on the epiglottis lifter. In this way, at least the detection side of the optical detection device, e.g. a lens, an objective or a camera, is arranged below the largely or completely closed region of the epiglottis lifter (so to speak under the roof) and is thus protected against the view being blocked by tongue tissue or by contamination.

The features of the intubation device are to be understood in the sense that the intubation device is suitable for guiding the endotracheal tube by way of its guide rail. Of course, it is also possible to use the intubation device to insert other tube-like objects into a patient, e.g. an endoscope. The guide rail can advantageously be rigid, and it is thus at least not substantially deformable when the intubation device is operated as intended.

The optical detection device may be designed in particular as a camera. With the intubation device inserted into the patient, the optical detection device permits an unimpeded view into the laryngeal inlet and the vocal cords.

In the unactuated state of the epiglottis lifter, the epiglottis lifter, at least in the region near the patient, is arranged on the upper face of the guide rail, e.g. by lying there on the guide rail. Advantageously, at an end remote from the patient, the epiglottis lifter can have an operating element for manual actuation by a user.

It can generally be said that, in the unactuated state of the epiglottis lifter, the patient-near region of the epiglottis lifter is located closer to the guide rail than in the actuated state. If the epiglottis lifter is actuated manually, for example by pulling on the operating element, the patient-near region of the epiglottis lifter is pulled away from the adjacent region of the guide rail.

The operating element can be configured in particular for receiving a tensile force upon actuation of the epiglottis lifter, in particular a tensile force directed away from the patient-near end. The user must therefore apply a tensile force to the operating element in order to actuate the epiglottis lifter.

The handle can be arranged on the lower face of the guide rail. The handle can protrude at a right angle with respect to the lower face of the guide rail or can be slightly inclined toward the end near the patient and thus be arranged obliquely with respect to the lower face of the guide rail, for example at an angle of between 60 and 90 degrees.

According to an advantageous embodiment of the invention, provision is made that the epiglottis lifter, at the patient-remote end of the largely or completely closed region, transitions into an open region, which has a slit-shaped recess bounded on each side (to the left and right of the slit-shaped recess) by a side web. In other words, an inner open longitudinal slit is formed between the side webs. Due to the inner open longitudinal slit, the guide channel is not covered and is thus freely accessible. The side webs can open into the operating element. In this way, the guide rail is not completely covered by the epiglottis lifter, and instead it is freely accessible through the longitudinal slit of the epiglottis lifter, in particular in a region remote from the patient. For example, in this region, the endotracheal tube can then be inserted through the longitudinal slit into the guide channel of the guide rail and be gripped by hand at the part of the endotracheal tube near the patient and advanced such that the endotracheal tube can be guided safely past the vocal cords and into the trachea.

According to an advantageous embodiment of the invention, provision is made that the epiglottis lifter, in the largely or completely closed region, is formed in a U-shape opposite to the guide rail. This achieves good stability and a high degree of stiffness of the epiglottis lifter. In addition, the unit composed of the guide rail and of the epiglottis lifter is very flat, so that it can be easily inserted into narrow airways. In this way, a universal intubation device can be created that is suitable for all sizes and age groups of patients, that is to say is suitable for all sizes of airways (one size fits all).

According to an advantageous embodiment of the invention, provision is made that the epiglottis lifter, at least in the largely or completely closed region, engages over the guide rail at both sides. The epiglottis lifter is therefore wider than the guide rail at least in this region. This permits a mechanically simple and reliable slide bearing of the epiglottis lifter on the guide rail.

According to an advantageous embodiment of the invention, provision is made that the epiglottis lifter is movable relative to the handle via the at least one bearing element, such that the epiglottis can be lifted during the intubation procedure by a relative movement of the epiglottis with respect to the handle. This permits ergonomically favorable operation. The entire unit composed of the guide rail and of the epiglottis lifter can be held by the user with one hand at the handle. To operate the epiglottis lifter, the position of the handle does not have to be changed; all that is needed is for the user to manually actuate the epiglottis lifter at the operating element using the other hand.

According to an advantageous embodiment of the invention, provision is made that the handle, at the end of the guide rail remote from the patient, is coupled rigidly to the guide rail. At least when the epiglottis lifter is actuated, there is no relative movement of the guide rail with respect to the handle.

According to an advantageous embodiment of the invention, provision is made that the epiglottis lifter is mounted slidably and/or pivotably on the guide rail via the at least one bearing element. This also promotes easy and ergonomic manual operation of the intubation device. For example, the epiglottis lifter can be slidable along a rectilinear or slightly curved region of the guide rail.

According to an advantageous embodiment of the invention, provision is made that the epiglottis lifter extends substantially over the entire longitudinal extent of the guide rail. The epiglottis lifter can also also extend beyond the guide rail at the end near the patient and/or at the end remote from the patient.

According to an advantageous embodiment of the invention, provision is made that the epiglottis lifter follows the shape of the guide rail in the longitudinal direction. Accordingly, the epiglottis lifter can lie closely on the guide rail over its entire longitudinal extent, such that the entire intubation device is particularly flat at least in the sections that are to be inserted into a patient.

According to an advantageous embodiment of the invention, provision is made that the unit composed of the guide rail and of the epiglottis lifter has over its entire longitudinal extent, at least in the unactuated state of the epiglottis lifter, an overall height that is less than 50% greater than the overall height of the guide rail at the respective location.

According to an advantageous embodiment of the invention, provision is made that the overall height of the unit composed of the guide rail and of the epiglottis lifter is less, over the entire longitudinal extent, than the width of this unit, in particular a maximum of 75% of the width.

According to an advantageous embodiment of the invention, provision is made that the epiglottis lifter is arranged and/or mounted on that side of the guide rail facing away from the handle, in particular in all adjustable positions of the epiglottis lifter that can be selected during intubation. This permits an ergonomically favorable use of the intubation device.

According to an advantageous embodiment of the invention, provision is made that the epiglottis lifter is movable steplessly or in a plurality of fine steps relative to the handle. This has the advantage that the epiglottis lifter can be positioned at any desired location, depending on the size of the patient's airways, as far as is necessary for opening the deep pharyngeal region and lifting the epiglottis. It is therefore not necessary to carry out a constructively specified minimum adjustment of the epiglottis lifter. This allows the intubation device to be used in a particularly universal and protective manner on patients with very different airways. In particular, the epiglottis lifter can be moved forward and backward steplessly or in fine steps relative to the handle, i.e. in both adjustment directions, so that the appropriate adjustment position can be easily found by testing. Adjustability in fine steps can, for example, include at least 10 or at least 20 steps. The epiglottis lifter can be movable in a latching manner along the guide rail.

According to an advantageous embodiment of the invention, provision is made that the intubation device has a first fixing device, with which a set relative position of the epiglottis lifter with respect to the handle is able to be fixed steplessly or in a plurality of fine steps. In principle, it is possible for a set relative position of the epiglottis lifter to be fixed by the user with one finger, for example a finger of the hand holding the handle. An additional mechanical fixing element, such as the first fixing device, can be used to ensure even safer and permanent fixing. In addition, handling can be made easier for the user by eliminating the need for the user to maintain the fixation manually. For example, the first fixing device can be formed similarly to a clamp or a clip, which is clamped over the guide rail and the epiglottis lifter.

According to an advantageous embodiment of the invention, provision is made that the epiglottis lifter is fastened detachably to a component of the intubation device so that, after the intubation procedure has been performed, the epiglottis lifter can be removed from the patient separately from the guide rail. This has the advantage that, after intubation, the individual parts of the intubation device can be removed from the patient separately from one another. The epiglottis lifter can be removed first, then the structural unit with the guide rail.

According to an advantageous embodiment of the invention, provision is made that the epiglottis lifter has at least one first form-fit fastening element which, at least in the unactuated state of the epiglottis lifter, is in form-fit engagement with a second form-fit fastening element of the intubation device. Accordingly, the epiglottis lifter is not just placed loosely on the guide rail; it is additionally fastened to it by the first form-fit fastening element. This prevents the epiglottis lifter from inadvertently coming loose and falling before insertion of the intubation device into the patient.

In this case, the first and second form-fit fastening elements are present in addition to the at least one bearing element. Advantageously, the first and second form-fit fastening element are in form-fit engagement with each other only in the unactuated state of the epiglottis lifter, i.e. they detach from each other after slight actuation of the epiglottis lifter, e.g. after an actuation path of less than 3 cm. This in turn is conducive to easy separation of the epiglottis lifter from the guide rail after intubation.

According to an advantageous embodiment of the invention, provision is made that the guide rail has, at least in a region near the patient, a bend section in which the guide rail is bent, when viewed from the side, e.g. convexly curved when viewed from the handle. For example, the bend section can include a 90 degree arc, or an arc of slightly more or less than 90 degrees, e.g. about 80 degrees. An advantageous example is a bend section that extends over an arc of 70 to 90 degrees. This is conducive to a targeted and rapid insertion of the guide rail into the airways of a patient, so that the patient is protected as much as possible.

According to an advantageous embodiment of the invention, provision is made that the guide channel on the inside of the bend section is largely or completely open. This is also conducive to a low-profile design of the intubation device. The guide channel can be largely or completely open on the upper face, even outside the bend section, even over the entire length. In particular, the guide rail can have a U-shaped profile at least in the bend section or overall.

According to an advantageous embodiment of the invention, provision is made that the guide rail, at the patient-remote end of the bend section, transitions into a linear or, by comparison with the bend section, less strongly curved section. This permits in particular a sliding linear guide or quasi-linear guide of the epiglottis lifter on the guide rail. The guide rail can have a much greater bending radius in the less strongly curved section than in the bend section.

According to an advantageous embodiment of the invention, provision is made that the intubation device has a second fixing device with which the position of the intubation device relative to the patient, in particular the angular position, can be fixed steplessly or in a plurality of fine steps. In particular, by means of the second fixing device, the tilt angle of the intubation device relative to the patient can be adapted. For example, the second fixing device can have a ball joint or universal joint, which can be fixed in a desired angular position, for example by means of a clamping device. For example, the second fixing device can be supported on the patient's jaw.

In this way, the intubation device introduced into the patient and fixed in a desired position can also take over the function of an oral airway. The airway is secured in this way with the intubation device, and the optical detection means advantageously provides a view into the airway, and thus the correct position can be safely confirmed.

The intubation device according to the invention combines an optimal viewing angle on the vocal folds with optimal guidance of a tube via the laryngeal inlet into the trachea. It is ideal for easier and safer securing of the airways by means of intubation for the difficult and normal airway. The intubation device according to the invention permits effective opening of the airways, reliable laryngoscopy and safe intubation in various clinical situations. Thus, the intubation device according to the invention offers a great many advantages:

1. Only the deep pharyngeal region is opened in such a way that the epiglottis is effectively lifted and a clear view of the entire laryngeal inlet is possible. The transverse diameter in the mouth and upper pharyngeal region is not further increased, and therefore no force or only very little force is applied there. In contrast to known devices, it is not necessary, for example, to bring the upper regions of the airways into line during or before opening the deep pharyngeal region and lifting the epiglottis, nor in particular to open and widen the mouth. In conventional laryngoscopy, but also in video laryngoscopy, a considerable pressure with application of a correspondingly high force is sometimes required for this purpose, which is why general anesthesia is then usually carried out, which is not necessarily required in the intubation device according to the invention.
2. On account of a very small distance between the patient-near end of the epiglottis lifter and the detection side of the optical detection device, the detection side can be positioned directly in front of the laryngeal inlet in order to obtain a full view of the glottis. In addition, the patient-near end of the epiglottis lifter can be guided around the tongue instead of displacing the latter.
3. Insertion into the mouth is facilitated by the unit composed of the guide rail and of the epiglottis lifter arranged thereon having a transverse diameter (overall height) of under 2 cm.
4. In most routine clinical cases, an optical detection device integrated in the guide rail and/or in the epiglottis lifter is effectively protected by the epiglottis lifter against visual blockage by upstream tongue tissue or against contamination caused by secretions or tongue coating.
5. The opening of the deep pharyngeal region and the lifting of the epiglottis is effected steplessly and, according to requirements, under visual monitoring.
6. The epiglottis lifter can be moved up and down again, and in this way the position can be corrected and adapted according to requirements under visual monitoring.
7. The guide rail and the epiglottis lifter can be easily and quickly separated from each other and easily removed from the mouth after intubation. This minimizes the risk of accidental extubation when removing the device immediately after intubation.
8. The optical detection device, critical for effective laryngoscopy with a full view of the glottis before, during and after intubation, is located on the guide rail. This view does not change when the deep pharyngeal region is opened, since the epiglottis lifter and the guide rail are moved independently of each other: This means that despite movements of the epiglottis lifter for opening the deep pharyngeal region and for lifting the epiglottis, the view of the glottis does not change, in accordance with the constant position of the guide rail.

The addition of an optical detection device on the epiglottis lifter is an add-on option for supportive monitoring, which is important in particular when there are changes in anatomy and large fluid accumulations.

9. Without restricting the freedom of movement or the other abovementioned properties of the epiglottis lifter, the opening or closing movement (see above at 5. and 6.) can be easily fixed under visual monitoring at the desired location. This can be achieved, for example, with a fastening clip. The optical monitoring ensures precise individual adjustment, which results in a very effective oropharyngeal airway.

10. When the intubation device is fixed in an open position, with the patient lying down, the weight of the tongue and of the soft-tissue parts of the throat presses the guide rail of the intubation device against the posterior wall of the throat and holds it independently in the set position. It is not necessary to secure it by hand or by other fixing means.

As can be seen, it is advantageous if the epiglottis lifter is adapted to the guide rail. When actuated, the epiglottis lifter can slide along and be guided by the guide rail. The guide rail thus has a double guiding function, namely firstly to guide the intubation tube and secondly to guide the epiglottis lifter. This guiding prevents the epiglottis lifter from slipping off sideways from the guide rail. Otherwise, the epiglottis lifter can be mounted more or less loosely on the guide rail, e.g. by the epiglottis lifter being held on the guide rail only by the fixing provided via the first and second form-fit fastening elements in the region of the unactuated position.

With regard to the curved shape in the bend section of the guide rail, the epiglottis lifter can also be adapted to this, e.g. by having a region which is curved in a side view and extends over an arc section of 70 to 90 degrees. In this curved region, the epiglottis lifter can be designed to be largely or completely closed and can thus form the aforementioned roof over the guide rail. The curved region can be adjoined by what, in a side view, is a straight region of the epiglottis lifter. The largely or completely closed section of the epiglottis lifter can end at the transition to the straight region or can extend somewhat, e.g. by a maximum of 4 cm, into this straight region. This is followed, in the direction of the patient-remote end, by the section which is formed with the side webs, and with the slit-shaped recess formed between the side webs, and which then transitions into the operating element. The side webs can be designed in cross section as a single angled profile.

In the context of the present invention, the indefinite article "a" or "an" is not to be understood as meaning a number. For example, if mention is made of a component, this is to be interpreted in the sense of "at least one component". Insofar as angle specifications are given in degrees, they refer to a circular dimension of 360 degrees (360°).

The invention is explained in more detail below with reference to exemplary embodiments and using drawings.

Figure 4:
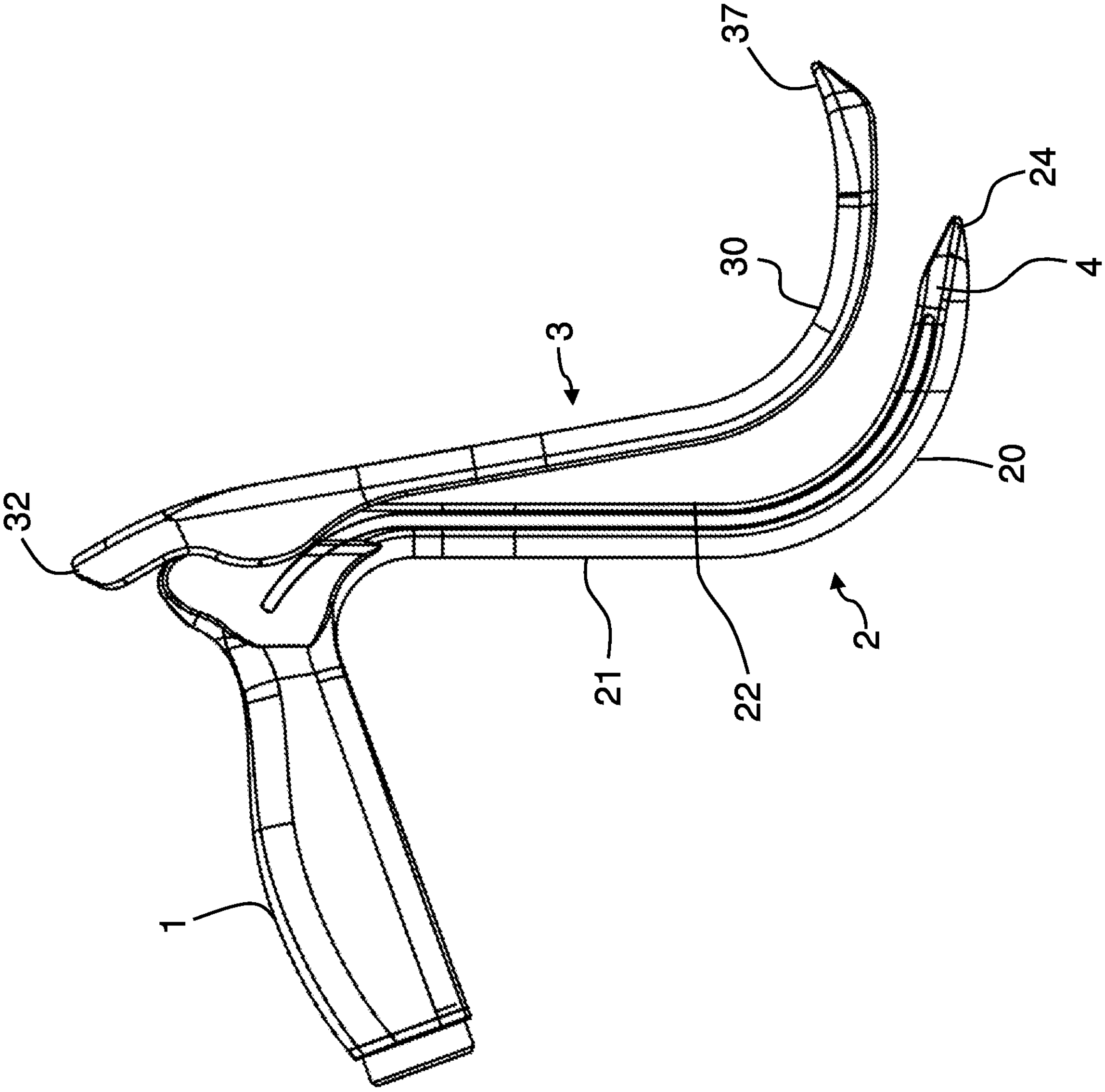
Figure 6:
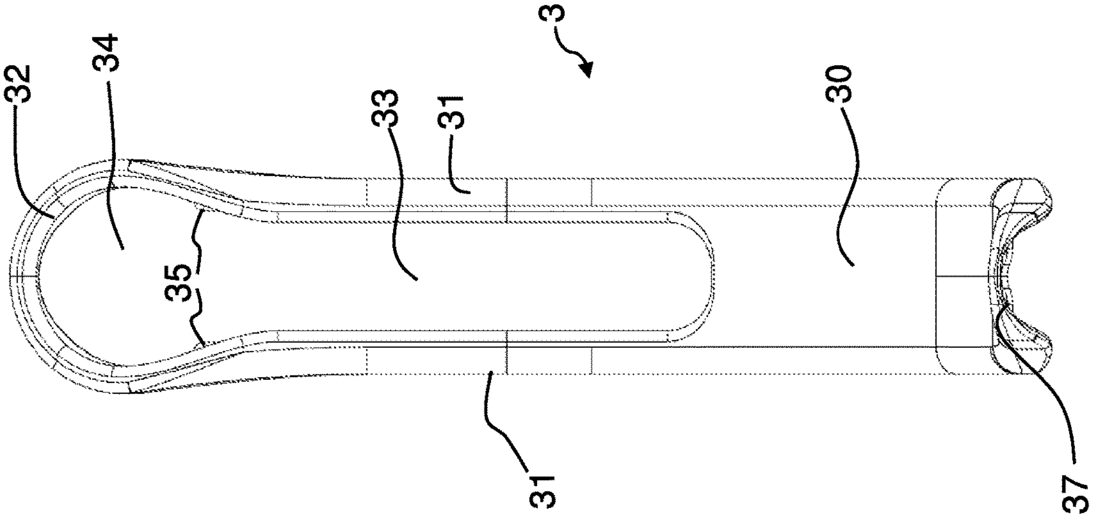
Figure 5:
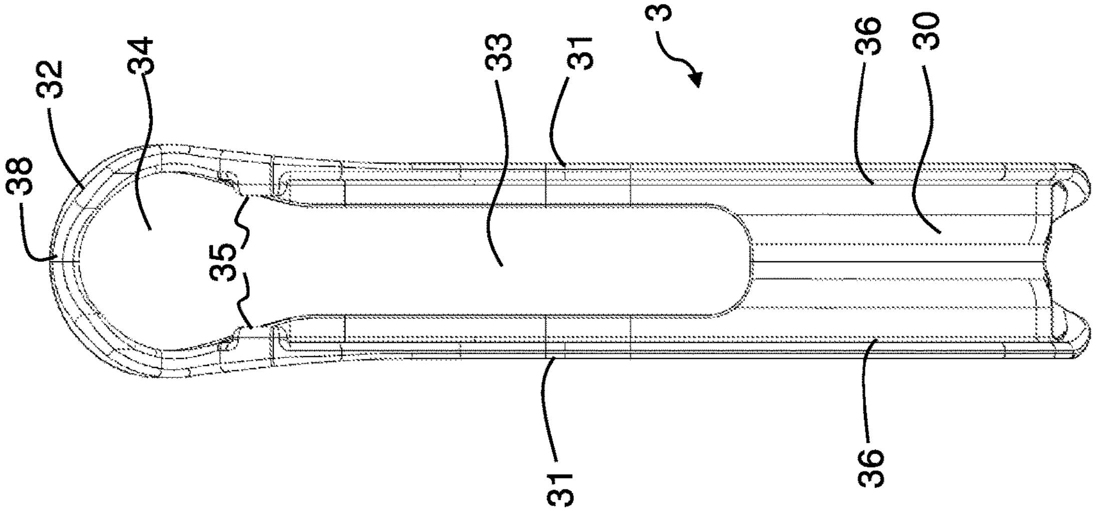
Figure 8:
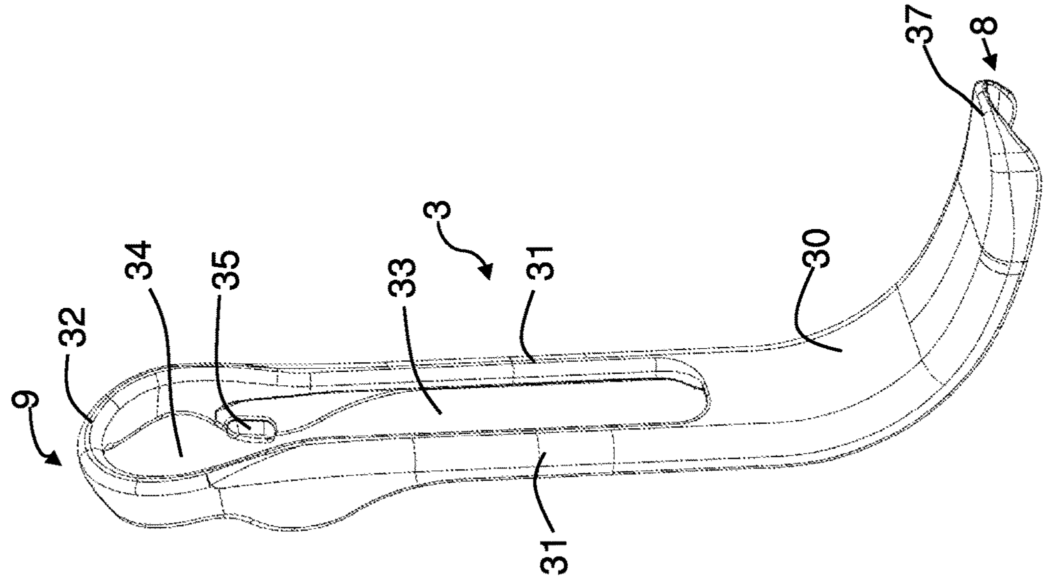
Figure 7:
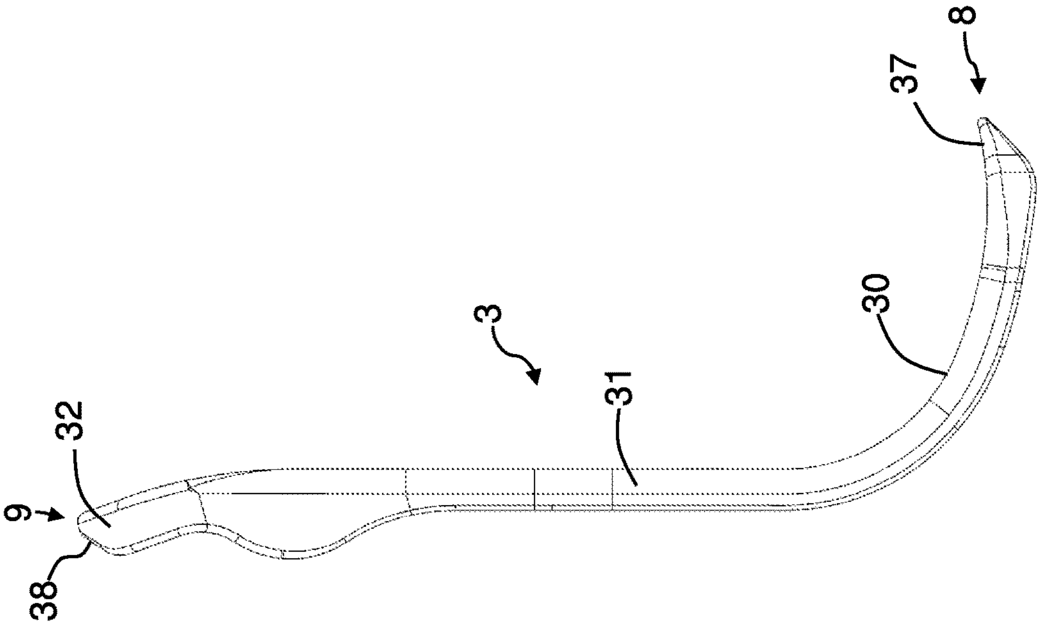
Figure 10:
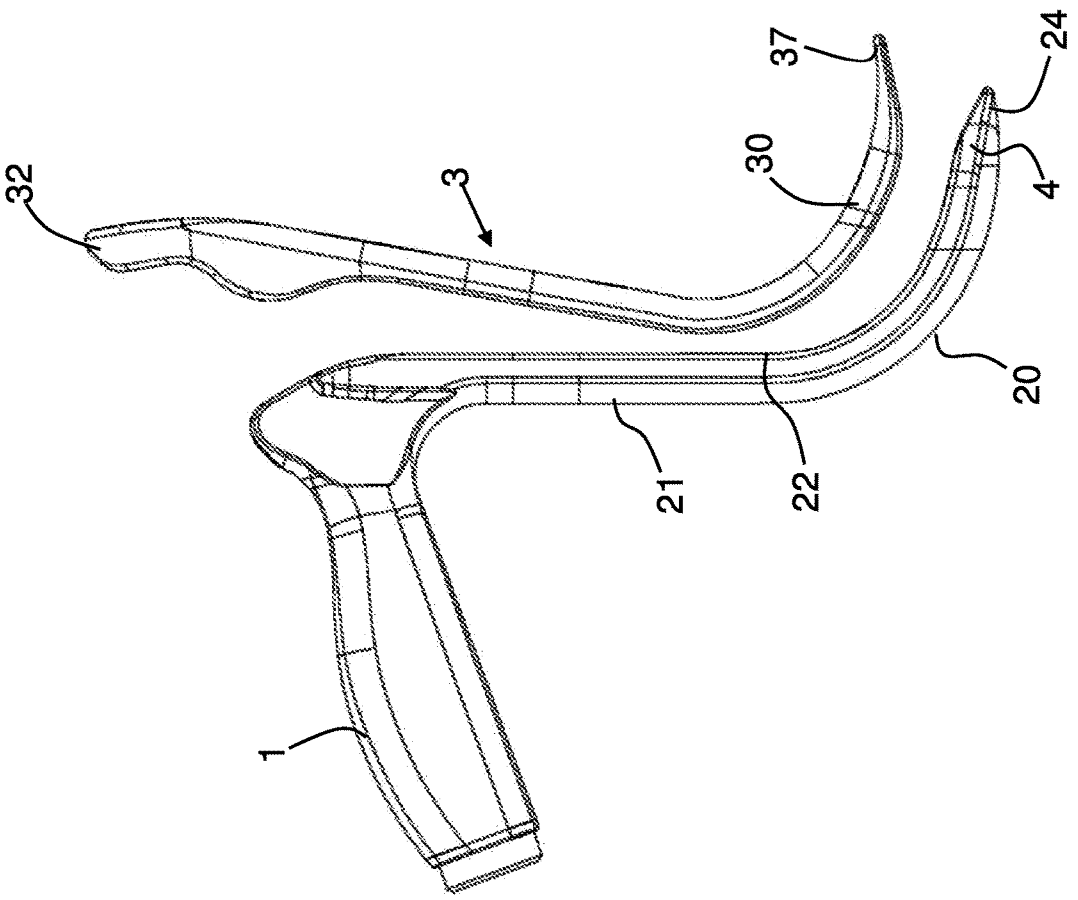
Figure 9:
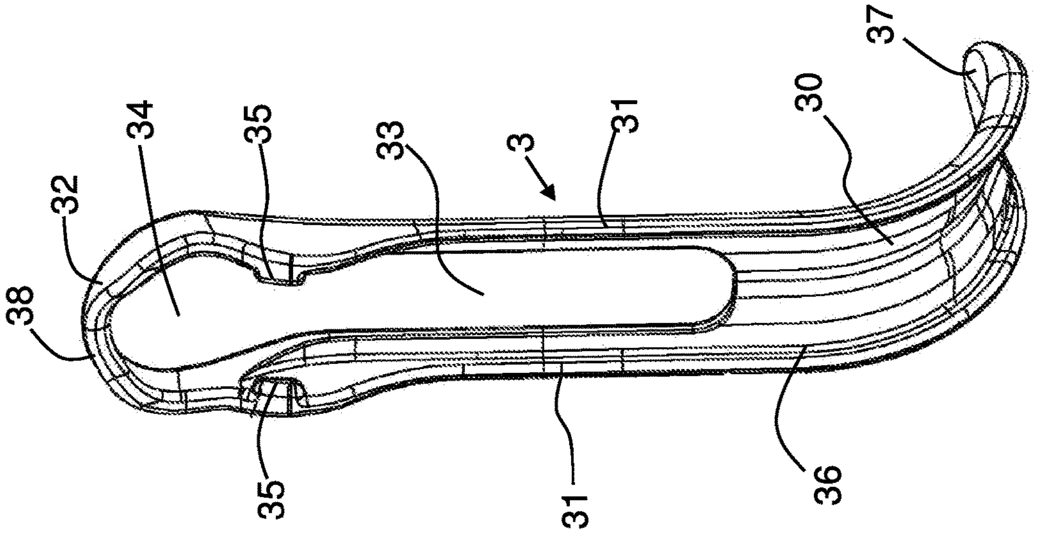
Figure 12:
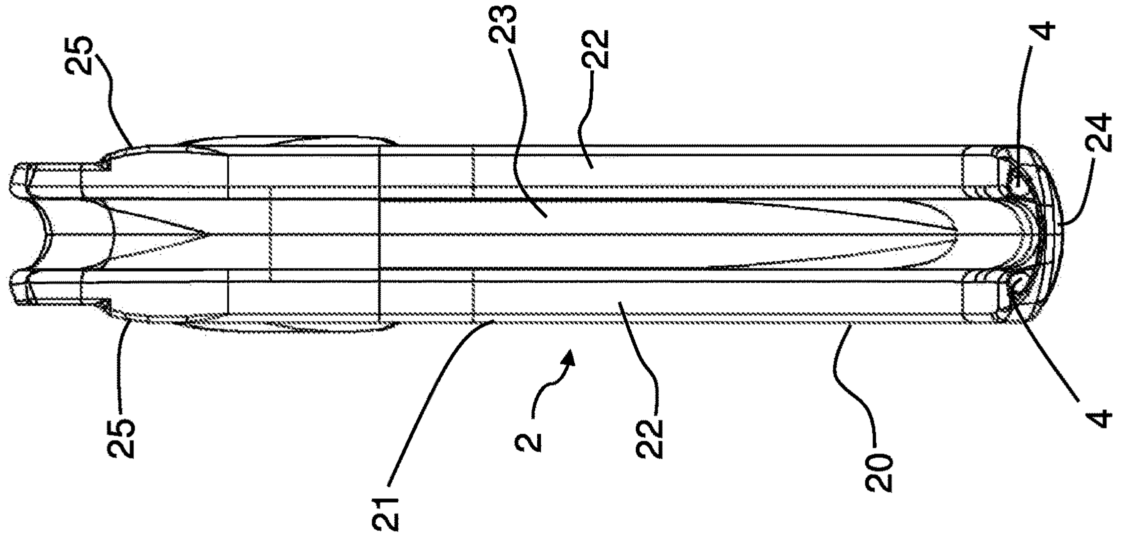
Figure 11:
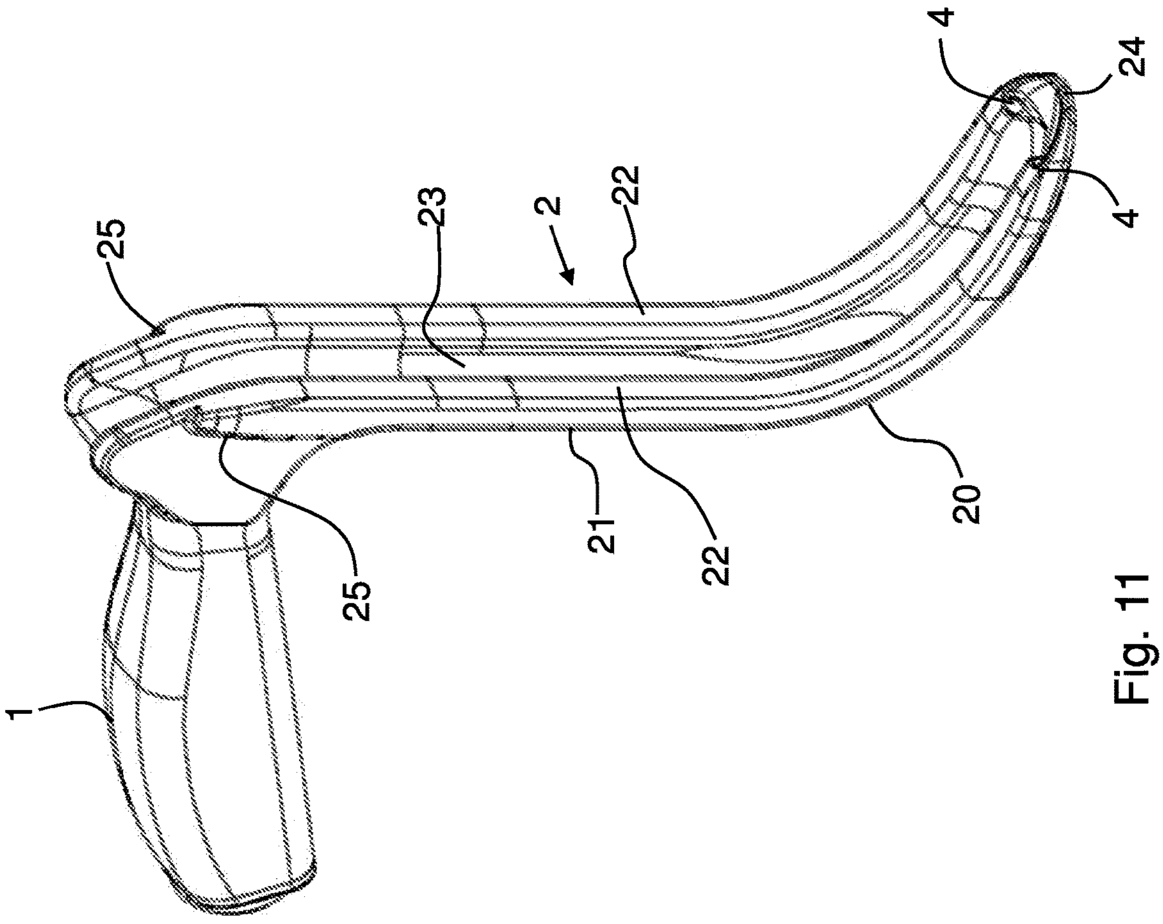
Figure 13:
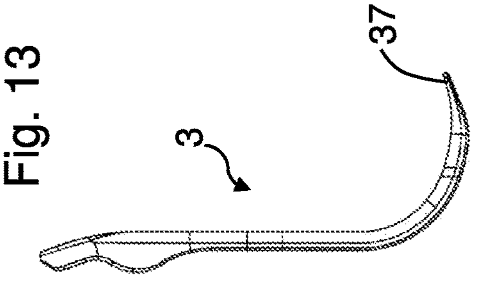
Figure 14:
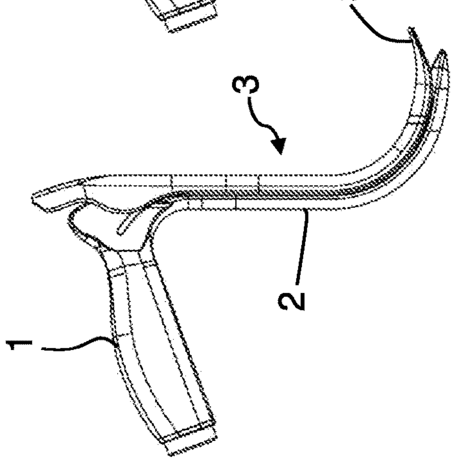
Figure 15:
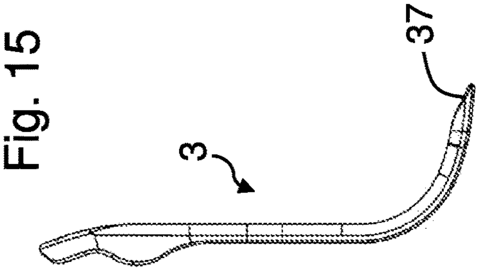
Figure 16:
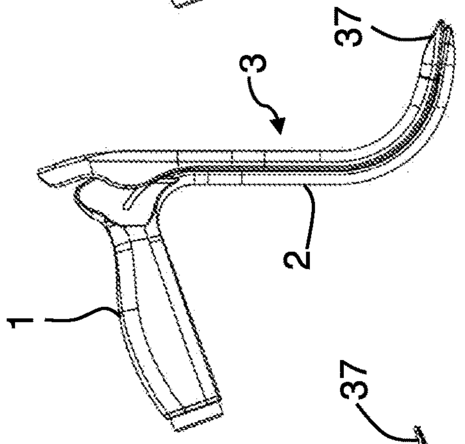
Figure 17:
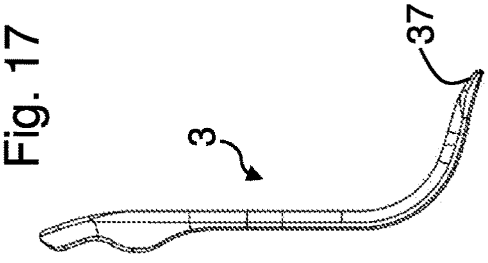
Figure 18:
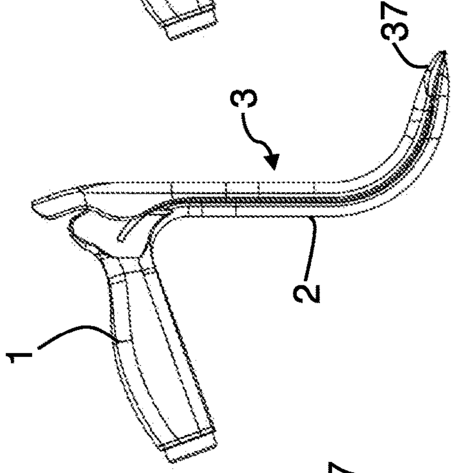
Figure 19:
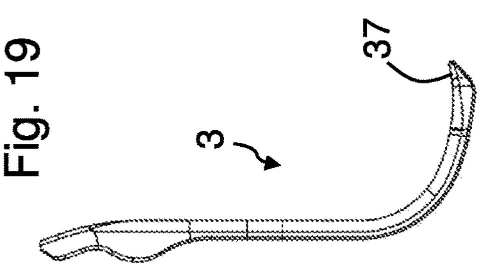
Figure 20:
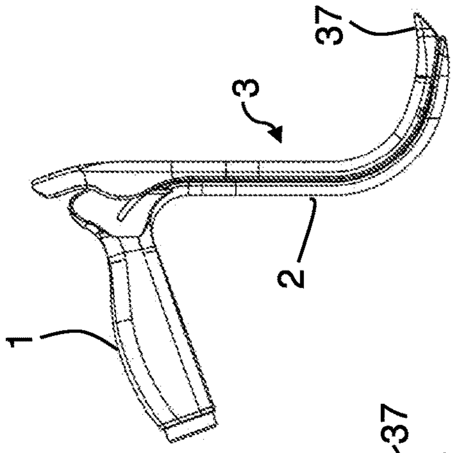

FIG. 4 shows the intubation device in a side view in another actuated state, FIG. 5 shows the epiglottis lifter in a view of the lower face, FIG. 6 shows the epiglottis lifter in a view of the upper face, FIG. 7 shows the epiglottis lifter in a side view, FIG. 8 shows the epiglottis lifter in a perspective view of the upper face, FIG. 9 shows the epiglottis lifter in a perspective view of the lower face, FIG. 10 shows the intubation device in a side view upon detachment of the epiglottis lifter, FIG. 11 shows the intubation device without epiglottis lifter in a perspective view of the upper face, FIG. 12 shows the intubation device without epiglottis lifter in a top view, FIGS. 13-20 show further embodiments of intubation devices and epiglottis lifters, each in a side view.

Figure 2:
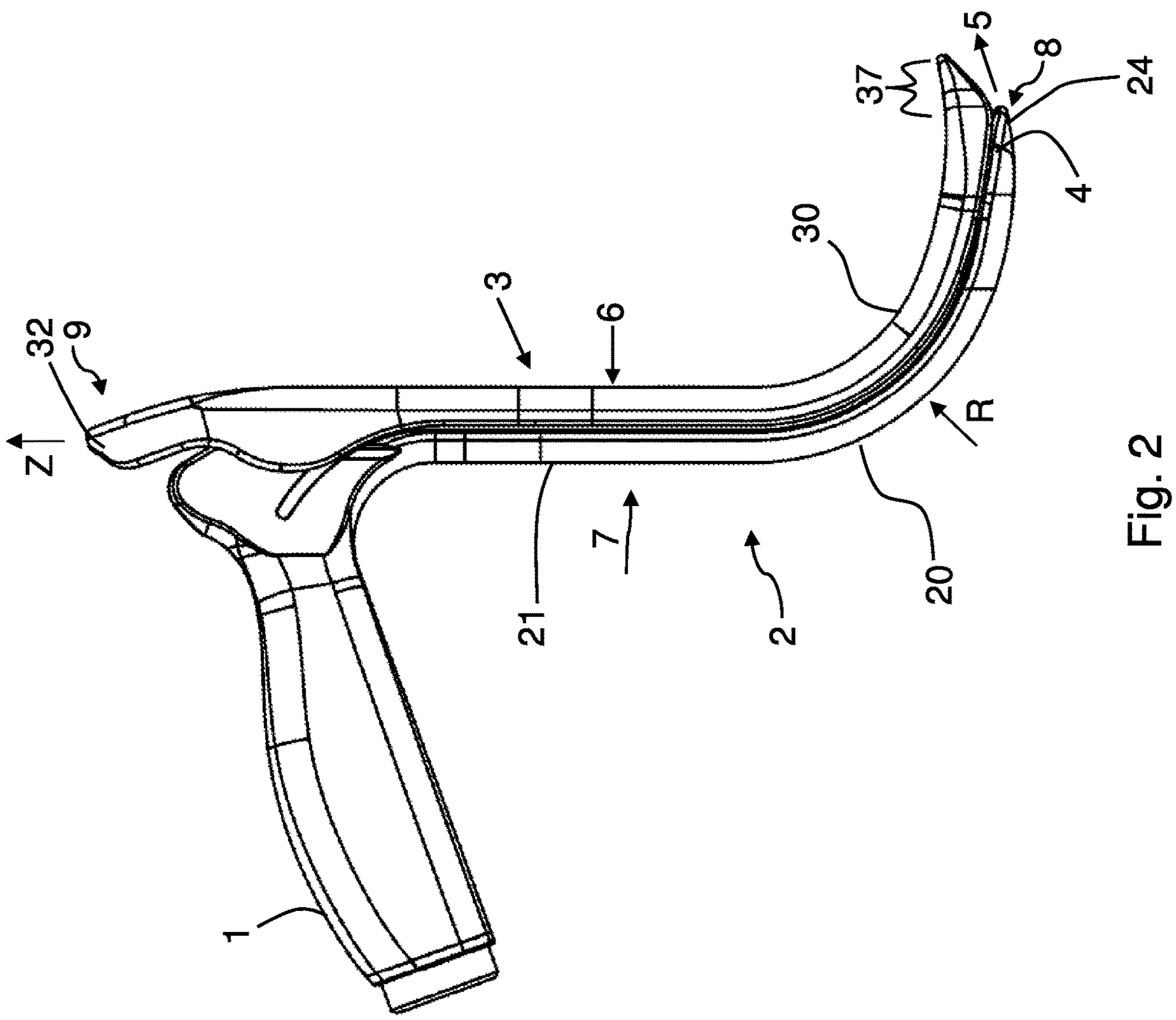
FIG. 2 shows the intubation device in a side view in the unactuated state.
Figure 1:
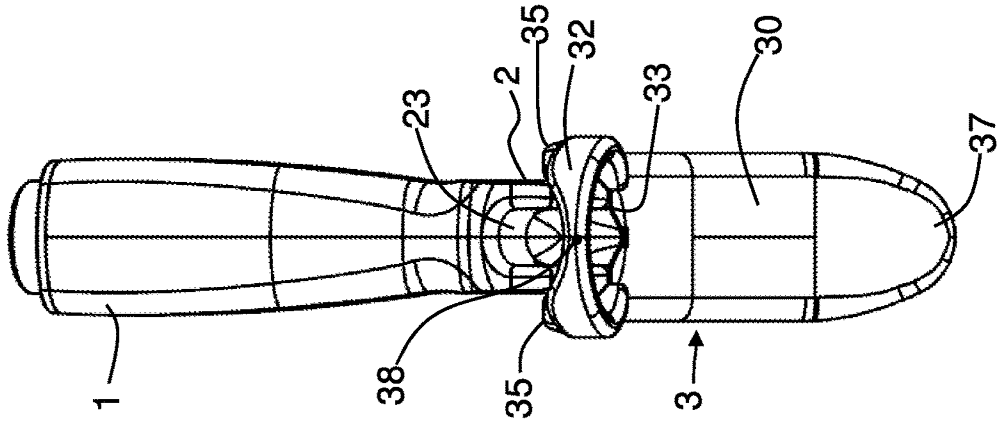
FIG. 1 shows an intubation device in a rear view.

The intubation device shown in FIGS. 1 and 2 has a handle 1 for holding the intubation device. The intubation device can be guided using the handle 1, in particular during the intubation. The handle 1 is configured such that it can be gripped by the user with the whole hand. The intubation device has a rigid guide rail 2, which is also connected rigidly to the handle 1. The handle 1 protrudes from a lower face 7 of the guide rail 2 and forms an angle of less than 90 degrees to the lower face 7 of the guide rail 2, for example an angle in the region of 70 degrees. In this way, the handle 1 is slightly inclined toward the patient-near region 8 of the guide rail 2.

In the patient-near region 8, the guide rail 2 ends with a bend section 20, in which the guide rail 2, in a side view, is curved with a certain radius R. Near the free end 24 of the guide rail 2, an optical detection device 4 is integrated into the guide rail 2. The bend section 20 can extend over an angle range of, for example, 70 to 100 degrees, with an angle of slightly less than 90 degrees being particularly advantageous. Seen from patient-near region 8, the bend section 20 is adjoined by a region 21 of the guide rail 2 that is straight when seen in a side view. This straight region 21 leads into the handle 1. The guide rail 2 is U-shaped in cross section and is accordingly open toward the upper face 6. A guide channel 23 extends over the entire longitudinal extent of the guide rail 2, in which guide channel 23 an endotracheal tube can be guided along the guide rail 2. The guide channel 23 is delimited to the left and right by raised edge sides of the guide rail 2.

An epiglottis lifter 3 is arranged on the upper face 6 of the guide rail 2. As can be seen in particular in FIG. 2, the epiglottis lifter 3 substantially follows the shape of the guide rail 2, that is to say the epiglottis lifter 3, in the straight region 21 of the guide rail 2, is likewise substantially straight. In the bend section 20 of the guide rail 2, the epiglottis lifter 3 is similarly curved. Only at the free end near the patient can the epiglottis lifter 3 be continued with a different shape. In particular, it can protrude slightly beyond the free end 24 of the guide rail 2 in the patient-near region 8.

As is illustrated particularly by FIGS. 5 to 9, the epiglottis lifter 3 is designed in the patient-near region 8 with a closed section 30, such that it forms a kind of roof over the upwardly open guide rail 2 and in this region is arranged in an opposite U-shape on the guide rail 2. In the direction of the patient-remote region 9, the closed section 30 of the epiglottis lifter 3 is adjoined by a partially open section, which is formed by side webs 31 arranged on the left and right of the guide rail 2. Between the side webs 31 there is a slit-shaped recess 33, through which the guide channel 23 is accessible. The side webs 31 open, in the patient-remote region 9, into an operating element 32 of the epiglottis lifter 3, which element, as can be seen, is of annular shape.

Within the annular operating element 32 there is an operating recess 34, in which the operating element 32 can be gripped by the user, e.g. with the thumb and the index finger. Advantageously, the dimension (diameter) of the annular operating element 32 or of the clearance created by the operating recess 34 is slightly wider than the guide rail 2. This allows the complete endotracheal tube with connector to be passed through the operating recess 34. The epiglottis lifter 3 can have a taper 38, facing in the direction of the handle 1, at the center of the upper edge of the operating element 32, which taper allows the insertion of the endotracheal tube or of a catheter also from the side of the epiglottis lifter 3 facing the handle 1 directly onto the guide rail 2, without passing through the slit-shaped recess 33 of the epiglottis lifter 3.

With their surfaces that face toward the epiglottis lifter 3, the raised edge sides delimiting the guide channel 23 to the left and right form support surfaces 22 for supporting the epiglottis lifter 3, as can be seen in FIGS. 11 and 12. The epiglottis lifter 3 is supported with its side webs 31 on the support surfaces 22 and can be slidably moved thereon. For this purpose, on the sides facing toward the guide rail 2, the side webs 31 have support surfaces 36, which rest on the support surfaces 22. The support surfaces 22 thus form bearing elements for the epiglottis lifter 3. The epiglottis lifter 3 can be slightly wider than the guide rail 2 and can accordingly overhang the guide rail 2 externally. This provides a reliable rail-like longitudinal guide of the epiglottis lifter 3 on the guide rail 2.

Furthermore, first form-fit fastening elements 35, for example in the form of inwardly protruding pins or protuberances, are integrally formed to the left and right on the epiglottis lifter 3, on the inner sides of the side webs 31 or in the transition to the operating element 32. Furthermore, in this region, second form-fit fastening elements 25 are located on the guide rail 2, which fastening elements can be arranged, for example, in the region of the transition of the guide rail 2 to the handle 1, for example in the form of outwardly protruding pins or protuberances. The second form-fit fastening elements 25, at least in the unactuated position of the epiglottis lifter 3 as shown in FIGS. 1 and 2, are in form-fit engagement with the first form-fit fastening elements 35 in order to hold the epiglottis lifter 3 on the guide rail 2. By virtue of this form-fit fixation, the epiglottis lifter 3 cannot be moved in particular in a direction away from the upper face 6 of the guide rail, that is to say it cannot be moved to the right in the view in FIG. 2.

Figure 3:
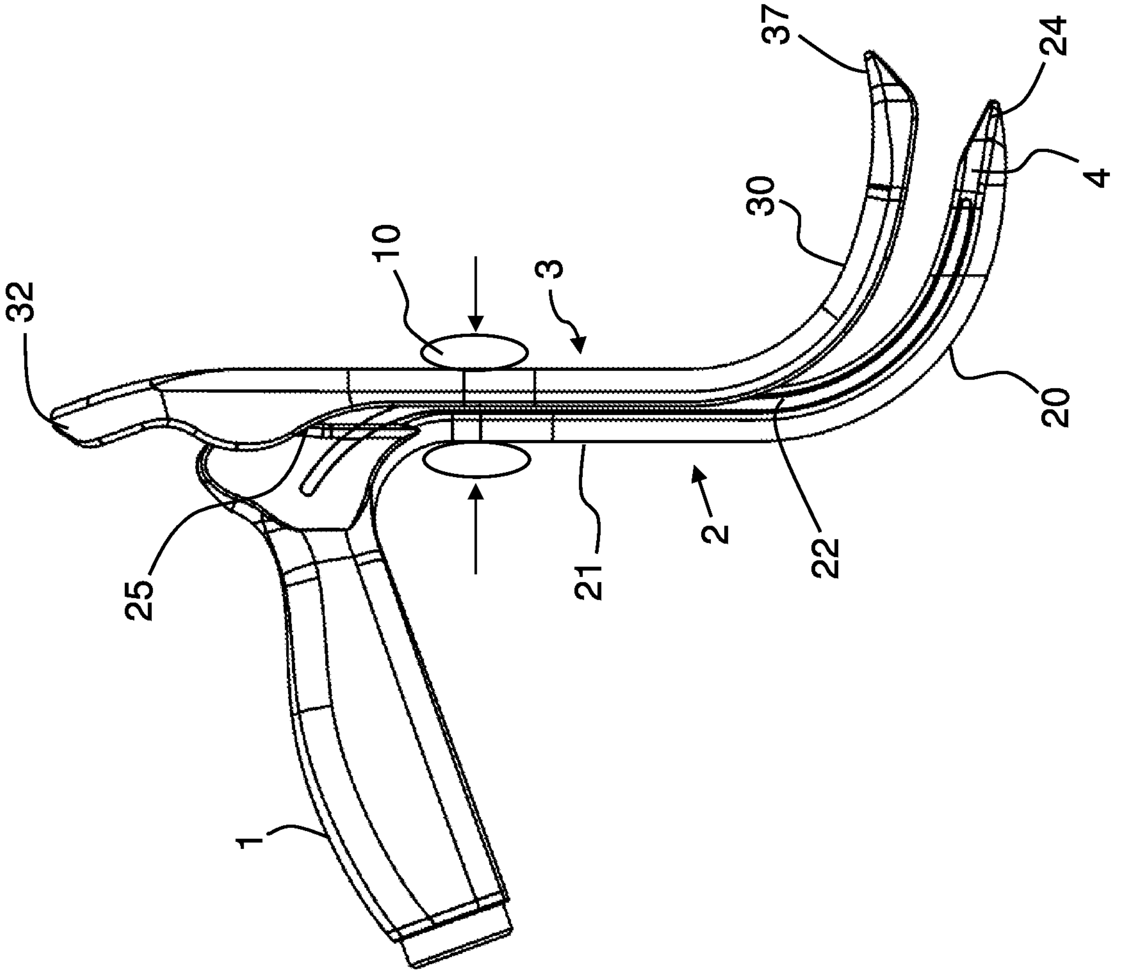
FIG. 3 shows the intubation device in a side view in the actuated state.

If the epiglottis lifter 3 is actuated by application of a tensile force Z to the operating element 32, it moves slightly upward in the view in FIG. 2, that is to say the curved patient-near region 30 of the epiglottis lifter 3 then moves away from the bend section 20 of the guide rail 2. In its straight region, the epiglottis lifter 3 slides along the straight region 21 of the guide rail 2. FIG. 3 shows the intubation device with the epiglottis lifter 3 actuated in this manner. From a certain actuation position, the form-fit fastening elements 25, 35 are then no longer in contact with each other, such that the epiglottis lifter 3 can be folded away from the guide rail 2, for example, by means of a pivoting movement, for example after carrying out the intubation procedure, when the epiglottis lifter 3 is to be removed from the patient.

As FIG. 3 likewise shows, the epiglottis lifter 3 can be fixed to the guide rail 2, in the actuated position in which the deep pharyngeal region of a patient is opened, with a first fixing device 10, such that the position is held. By the first fixing device 10, the epiglottis lifter 3 is pressed against the guide rail 2, as is illustrated by the arrows in FIG. 3.

FIG. 4 shows an alternative possibility of actuating the epiglottis lifter 3 in the form of pivoting or tilting the epiglottis lifter 3 relative to the guide rail 2. For this purpose, the epiglottis lifter 3 is mounted pivotably on the guide rail 2. By actuation of the operating element 32, the part of the epiglottis lifter 3 near the patient is pivoted away from the guide rail 2.

In the actuated position, as shown in FIG. 3 for example, the epiglottis lifter 3 can be removed from the guide rail 2, as illustrated in FIG. 10.

Opening Exclusively of the Deep Pharyngeal Region

The epiglottis lifter 3 is precisely adapted to the guide rail 2. If the epiglottis lifter 3 slides upward by actuation on the operating element 32 with the tensile force Z on the guide rail 2, the distance between guide rail 2 and epiglottis lifter 3 increases only in the lower patient-near region 8, whilst in the upper patient-remote region 9 the low overall height is retained. This opens the deep pharyngeal region and exposes the laryngeal inlet by lifting the epiglottis.

For example, the epiglottis lifter 3 is pulled upward with the left hand and held in the desired position with the right hand, which also holds the handle 1: For this purpose, the thumb and index finger of the left hand pull on the operating element 32 with the tensile force Z. This causes the epiglottis lifter 3 to slide upward along the guide rail 2, and the deep pharyngeal region is opened. With the index finger of the right hand, the respective distance can be maintained steplessly, in the manner required, and safely. For this purpose, the index finger of the right hand presses the epiglottis lifter 3 against the guide rail 2, while the handle 1 is held with the thumb and other fingers of the right hand.

These two individual components are applied simultaneously in a coordinated manner: The epiglottis lifter 3 slides upward on the guide rail 2 under the tip of the index finger during lifting. If the epiglottis lifter 3 is pressed against the guide rail 2 with the tip of the index finger, the desired position is thereby fixed and is also securely maintained during intubation.

The pulling up with the left hand and holding with the right hand take place at the same time. With optical monitoring by means of the optical detection device 4, the desired height can thus be adjusted steplessly and according to requirements and can also be maintained without any problems during intubation.

Length and Curvature of the Blade Tip 37

The blade tip 37 is understood to be the end of the epiglottis lifter 3 near the patient (the distal end from the point of view of the user). By virtue of a very small distance between blade tip 37 and optical detection device 4, in comparison with all other video laryngoscopes, the optical unit can be positioned directly in front of the laryngeal inlet. From this position, in contrast to the current state of the art, the entire glottis can be viewed, since it is possible to see past the arytenoid cartilage, the epiglottis and the tube. Instead of loading the tongue and displacing it upward to make room for laryngoscopy and intubation, as is the case with standard laryngoscopy, this comparatively small blade tip 37 is guided around the tongue.

In addition to its length, the angle of curvature of the blade tip 37 is of great importance for the proper functioning of the entire system: The blade tip 37 can advantageously be curved upward by approximately 10°, i.e. can protrude upward by approximately 10° relative to the lower face of the guide rail 2 in this region. This ensures the following two functions: 1. The pulling-up of the epiglottis lifter 3 also leads to reliable and effective erection of the epiglottis, even in tall patients of over 180 cm. 2. The angle of curvature and the resulting opening between the blade tip 37 and the free end 24 of the guide rail 2 are still small enough to be able to guide the two tips 24, 37 around the tongue in the unactuated state of the epiglottis lifter 3. The greater the angle and the resulting pincer-shaped opening, the greater the risk that the ends 24, 37 are not guided around the tongue, but into the root of the tongue, instead of further into the larynx. Then, even when the epiglottis lifter 3 is pulled up, no view of the glottis can be obtained, since tongue tissue further blocks the view.

As FIG. 2 shows, the blade tip 37 protrudes slightly, e.g. about 1 cm, beyond the free end 24 of the guide rail 2 and has an angle of curvature of 10° relative to the lower face of the guide rail 2. The smaller the length and angle of curvature of the blade tip 37, the easier it is to guide the better adapted ends 24, 37 of guide rail 2 and epiglottis lifter 3 around the tongue.

FIGS. 13 to 20 illustrate variants of the epiglottis lifter 3. FIGS. 13, 15, 17 and 19 each show only the epiglottis lifter 3, while the respective FIGS. 14, 16, 18 and 20 shown below these show the entire intubation device together with the epiglottis lifter 3 that is shown above. The blade tips 37 of the variants in FIGS. 15 to 18 do not protrude, or protrude only very little, beyond the guide rail 2, and they are also not curved upward like the standard variant in FIGS. 13 and 14, but downward toward the guide rail 2. Thus, in FIGS. 15 to 18, the ends of guide rail 2 and epiglottis lifter 3 are, like the upper and lower jaw of a dolphin, better adapted and the opening closed. This facilitates passage around the tongue and in particular around the tongue floor.

However, with this straight, flattened form of the blade tip 37, the epiglottis is raised to a lesser extent and, above all, not so reliably. This is even more clearly the case with increasing body size. This can make it difficult to see the glottis and thus also to perform the intubation.

Transverse Diameter and Other Lifting Mechanisms

Due to the shape of the protruding blade tip 37, a small overall diameter is also achieved in this region, and thus the insertion is also guaranteed even with a small mouth opening. As has already been shown above, as a result of the operating principle of the epiglottis lifter 3, the transverse diameter at the mouth and in the upper pharyngeal region remains below 2 cm even after opening the airway. If the epiglottis lifter 3 is not moved as illustrated in FIG. 3, but tilted or pressed down as illustrated in FIG. 4, the diameter is increased not only in the lower pharyngeal region, but also in the upper pharyngeal region. As a result, increased force has to be applied, and opening cannot take place as effectively.

Here, other mechanisms are advantageous that minimize or prevent the increase in the transverse diameter in the upper pharyngeal region. Besides the above-described method of upward pulling, this can also be achieved by moving the pivot point further downward. In addition, the lower region can also be opened using a tilting blade, without having to further open the transverse diameter in the upper region.

Protection of the Optical Detection Device 4—"Roof" and Side Edges

The important functions ensured by the protruding blade tip 37 and by the angle of curvature have been described above. This shape of the blade tip 37 also keeps secretions and tongue tissue at a distance, and visual blockages of the optical detection device 4 in the guide rail 2 can be prevented in most cases.

In addition, the protection of the optical unit in the guide rail 2 is ensured by laterally rounded edges and, above all, by a "roof" in the region 30 of the epiglottis lifter 3. The epiglottis lifter 3 can have a closed configuration from the blade tip 37 to the lower third. This prevents soft tongue tissue from reaching the optical unit, especially under anesthesia or in a coma, and partially or completely obstructing the view. Even without upward pulling, the curvature and shape of the blade tip 37 ensure a clear view and also free passage of an endotracheal tube with an external diameter of up to 10 mm.

Stepless Lifting of the Epiglottis Lifter 3

As described above, the opening of the deep pharyngeal region and the lifting of the epiglottis with the epiglottis lifter 3 take place steplessly and, according to requirements, under visual monitoring. For this purpose, the desired position of the epiglottis lifter 3 can be fixed and held at any time by changing the pressure applied to the guide rail 2, for example with the tip of the index finger when pulling upward with the other hand. This function can also be taken over by a fastening ring or another first fixing device 10.

Change of Direction During Movements of the Epiglottis Lifter 3

If necessary, the epiglottis lifter 3 can be moved not only up, but also down again, thus correcting the position under visual monitoring and adjusting it as desired. Such corrections of direction are particularly necessary when the epiglottis lifter 3 is to be moved back to the starting position. This is the prerequisite for being able to pull it out of the mouth again when in the closed state together with the guide rail 2. This becomes necessary when intubation is to be performed with another tube or when intubation is not performed, but instead a different intervention. For example, this includes the administration of local anesthesia to the laryngeal inlet. Pulling out the entire closed intubation device is then easier than separating epiglottis lifter 3 and guide rail 2 and removing them individually, as is required after an intubation.

Anchoring, Tube Guiding, and Separation of Tube, Epiglottis Lifter and Guide Rail When removing the intubation device after intubation, accidental extubation must be almost certainly excluded. For this purpose, the epiglottis lifter 3 is very easily and quickly separated from the guide rail 2: To do this, the epiglottis lifter 3 is pulled even further upward, wherein it is released from its fixation to the guide rail 2 caused by the form-fit fastening elements 25, 35. It is then guided forward in order to pull it out of the mouth.

The fixing means is, for example, an approximately 10 mm long protuberance on the epiglottis lifter 3, which is guided behind a protuberance at the upper edge of the guide rail 2. This results in a loose connection, but one that is sufficient to prevent accidental detachment of the epiglottis lifter 3 from the guide rail 2. It is only when the protuberance of the epiglottis lifter 3 is pulled over the corresponding edge of the guide rail 2 that the anchoring between epiglottis lifter 3 and guide rail 2 loosens. This simple mechanism means that the epiglottis lifter 3 does not have to be actively held on the guide rail 2. This anchoring prevents the epiglottis lifter 3 from accidentally detaching itself from the guide rail 2 again, especially when the intubation device is inclined forward. On the other hand, this simple fixing ensures that, as described above, the connection between epiglottis lifter 3 and guide rail 2 can be quickly and easily released again by simply pulling upward.

At the same time, the epiglottis lifter 3 is also easily and quickly separated from the endotracheal tube when the anchoring is released by pulling it upward and tilting it forward. This makes accidental removal of the endotracheal tube very unlikely. Advantageous for this is the recess 33 reaching from the lower third of the epiglottis lifter 3 to the operating element 32: Through this opening, the endotracheal tube is inserted into the guide channel 23 prior to intubation and clamped between guide rail 2 and epiglottis lifter 3. During intubation, this recess 33 ensures that the endotracheal tube can be gripped in its middle region and can also be advanced into the trachea by various maneuvers, such as rotational movements, even during problematic intubation procedures.

After the intubation, the e.g. at least 30 mm large operating recess 34 of the annular operating element 32 at the upper end of the epiglottis lifter 3 is then of special significance: This opening ensures that, after intubation, the wide ventilation connector of the endotracheal tube can be easily inserted and thus the endotracheal tube can be separated from the epiglottis lifter 3. This minimizes the risk of accidental extubation.

Separation of epiglottis lifter 3 and endotracheal tube: The epiglottis lifter 3 is tilted forward, i.e. away from the guide rail 2 in the patient-remote region, wherein the endotracheal tube is guided through the operating recess 34 and thus separated from the epiglottis lifter 3. After the removal of the epiglottis lifter 3, the guide rail 2 is pulled out of the mouth using the handle 1, the endotracheal tube being held in position with the other hand.

Optical Unit in the Epiglottis Lifter and Fastening Mechanism for Optical Unit

The integration of an optical unit, i.e. of an optical detection device, in the epiglottis lifter 3 is an add-on option for providing supplementary monitoring. In certain situations, such supplementary monitoring can be useful in addition to one or two optical units located in the guide rail 2:

For example, to permit better orientation in cases where the anatomy has been modified by a malignant disease, an additional viewing perspective from further back and above can be advantageous. In addition, in the case of problematic viewing conditions, the position of the two lower optical units in the guide rail 2 relative to the anatomical structures can, in such difficult conditions, be better detected and, if necessary, corrected from this perspective. This may be of advantage not only in the case of modified anatomical conditions, but also for beginners.

However, such a position of the optical unit is especially advantageous if a lot of fluid accumulates in the lower pharyngeal region and cannot be aspirated effectively or quickly enough. This may be the case, for example, in the event of vomiting or pronounced bleeding. Even with an irrigation system providing powerful suction located at the lowest point under the guide rail, the view provided by the optical units in the guide rail may become blocked. In this special emergency situation, an optical unit located higher up in the epiglottis lifter may still ensure adequate visibility.

An optical unit can be permanently installed in the epiglottis lifter 3. However, an optical unit such as a disposable endoscope can also be fastened to the lower face of the epiglottis lifter 3: For this purpose, round brackets and/or a channel can be embedded in the epiglottis lifter 3. An endoscope can then be fastened in such a way that it is fixed in a rotationally stable manner at a certain point on the lower face. For example, this can be at the level of the optical units in the guide rail 2. Additional options for fastening to the epiglottis lifter ensure the rotational stability of the endoscope.

A fastening mechanism embedded in the lower face of the epiglottis lifter 3 for fastening an optical unit extends as little as possible downward into the guide channel 23. This is to ensure that the endotracheal tube slides unimpeded on the guide rail 2. This is also intended to avoid damage to the cuff, such as is often caused, for example, by the guide clips in the oropharyngeal airway after Ovassapian.

Fixation of the Epiglottis Lifter in the Actuated Position and Individually Adapted Oropharyngeal Airway A first fixing device 10, easy to attach and also to remove, fixes epiglottis lifter 3 and guide rail 2 in the upper part, i.e. in the patient-remote region 9, which is outside the patient during the intubation procedure. This fixing mechanism presses epiglottis lifter 3 and guide rail 2 together exactly in such a way that the epiglottis lifter 3 is, on the one hand, able to be moved further up and down freely and unrestricted. On the other hand, the pressure is sufficient to automatically fix the position adopted under visual monitoring. No additional pressure or activation of a further fixing mechanism is required.

The first fixing device 10 can be integrated in the epiglottis lifter 3 or, for example, can be guided as a separate fastening ring around epiglottis lifter 3 and guide rail 2 and fastened there. The attached first fixing device 10 can be guided upward according to requirements in the closed state, in order to be able to insert the guide rail 2 more deeply, especially in very large patients. The attached first fixing device 10 can also be guided downward in order to be able to fix the intubation device even more stably in different planes with an optimized view of the glottis, by means of a counter-pressure upon contact with the mouth or teeth.

As soon as the glottis view has been adjusted, the intubation device forms a safe, individually adapted oropharyngeal airway. It reliably keeps the airway open, because the optimal position for an oropharyngeal airway has been achieved when adjusting the view of the glottis: The epiglottis, tongue tissue and other airway structures attached to the posterior wall of the throat have been effectively lifted or opened. This not only enables safe intubation. This individually adapted and therefore optimal oropharyngeal airway keeps the upper airways safely and reliably open and thus ensures unobstructed breathing.

In addition, continuous suction of fluid at the lowest point of the throat can now be performed under visual monitoring, e.g. with a suction and irrigation system. Other measures can now also be performed on the reliably opened airways.

Independent Fixing of the Laryngoscopy Position in the Patient

As a result of the above-described fixing in an open position by means of the first fixing device 10, the intubation device no longer needs to be held or otherwise fixed, for example via a support or another retainer, in order to be able to perform interventions on the larynx. With the patient lying down, the fixing of the epiglottis lifter 3 on the guide rail 2 in the actuated position thus also automatically fixes the entire intubation device in the desired position, with the achieved setting for an optimized view of the laryngeal entrance: The weight of the tongue and of soft-tissue parts of the throat presses the guide rail 2 downward against the posterior wall of the throat. This means that the position with the set view of the glottis is held independently and safely. As has already been mentioned, securing by hand or any other form of fixing is no longer required.

The fixed, secure opening of the airways frees both hands from operating the intubation device. Therefore, interventions or measures can now be carried out without further assistance: For example, a flexible endoscope can be safely guided into the trachea without anyone having to keep the airways open. This takes place with a continued view of the glottis, even after insertion of the endoscope into the trachea.

In addition, there are specially curved surgical instruments for performing interventions on the larynx along the natural curvature of the airways. With the laryngoscope position fixed in the patient, these instruments can now be easily guided to the larynx. Since much less stress is caused by this much gentler form of opening the airways and by this fixing method, procedures that have hitherto been performed under general anesthesia can now be be carried out under much less stressful local anesthesia.

LIST OF REFERENCE SIGNS

1 handle
2 guide rail
3 epiglottis lifter
4 optical detection device
5 detection direction of the optical detection device
6 upper face of the guide rail
7 lower face of the guide rail
8 region near patient
9 region remote from patient
10 first fixing device
20 bend section of the guide rail
21 straight region of the guide rail
22 support surfaces of the guide rail
23 guide channel
24 free end (tip) of the guide rail 2
25 second form-fit fastening element
30 largely or completely closed section
31 side web
32 operating element
33 slit-shaped recess
34 operating recess
35 first form-fit fastening element
36 support surfaces of the epiglottis lifter
37 blade tip
38 taper
R radius of curvature of the guide rail 2 in side view
Z tensile force on the operating element 32

The invention claimed is:

1. An intubation device for intubating a patient with an endotracheal tube, comprising:

a) a handle for holding the intubation device, b) a guide rail connected to the handle, wherein the guide rail comprises a guide channel, wherein the guide rail extends in a longitudinal direction from a patient-remote end to a patient-near end, wherein the guide rail is configured for guiding the endotracheal tube, wherein the guide rail has an upper face configured for facing toward a patient's tongue during an intubation procedure, (c) an epiglottis lifter configured for lifting a patient's epiglottis, wherein the epiglottis lifter is mounted movably on a component of the intubation device via at least one bearing element, (d) at least one optical detection device in either or both a region of the patient-near end of the guide rail and/or on the epiglottis lifter in the region of the patient-near end of the guide rail, (e) wherein the epiglottis lifter, at least in the region of the patient-near end of the guide rail, covers and largely or completely closes the guide rail or at least the guide channel on the upper face of the guide rail, and wherein the epiglottis lifter at a region of the patient-remote end transitions into an open region.

2. The intubation device according to claim 1 wherein the epiglottis lifter, in the largely or completely closed region, is formed in a U-shape opposite to the guide rail.

3. The intubation device according to claim 1 wherein the epiglottis lifter, at least in the largely or completely closed region, engages over the guide rail at two sides of the guide rail.

4. The intubation device according to claim 1, wherein the epiglottis lifter is movable relative to the handle via the at least one bearing element, wherein the epiglottis lifter and the handle are configured such that a patient's epiglottis can be lifted during an intubation procedure by a relative movement of the epiglottis lifter with respect to the handle.

5. The intubation device according to claim 1, wherein the epiglottis lifter is mounted slidably and/or pivotably on the guide rail via the at least one bearing element.

6. The intubation device according to claim 1, wherein the epiglottis lifter is movable steplessly or in a plurality of fine steps relative to the handle.

7. The intubation device according to claim 1, further comprising a first fixing device for fixing a set relative position of the epiglottis lifter, wherein fixing is performed steplessly or in a plurality of fine steps.

8. The intubation device according to claim 1, wherein the epiglottis lifter has at least one first form-fit fastening element which, at least in an unactuated state of the epiglottis lifter, is in form-fit engagement with a second form-fit fastening element, wherein the second form-fit fastening element is associated with the intubation device but not with the epiglottis lifter.

9. The intubation device according to claim 1, wherein the guide rail, at least in a region of the patient-near end, has a bend section in which the guide rail has a convex curvature, as viewed from a side on which the handle is arranged.

10. The intubation device according to claim 9, wherein the guide channel on an inside of the bend section is largely or completely open.

11. The intubation device according to claim 9 wherein the guide rail, at the patient-remote end of the bend section, transitions into a linear or, by comparison with the bend section, less strongly curved section.

12. The intubation device of claim 1, wherein the guide rail comprises a bend section, and wherein the epiglottis lifter covers the guide rail in the bend section.

13. An intubation device for intubating a patient with an endotracheal tube, comprising:

a) a handle for holding the intubation device, b) a guide rail connected to the handle, wherein the guide rail comprises a guide channel, wherein the guide rail extends in a longitudinal direction from a patient-remote end to a patient-near end, wherein the guide rail is configured for guiding the endotracheal tube, wherein the guide rail has an upper face configured for facing toward a patient's tongue during an intubation procedure, (c) an epiglottis lifter configured for lifting a patient's epiglottis, wherein the epiglottis lifter is mounted movably on a component of the intubation device via at least one bearing element, (d) at least one optical detection device in either or both a region of the patient-near end of the guide rail and/or on the epiglottis lifter in the region of the patient-near end of the guide rail, (e) wherein the epiglottis lifter, at least in the region of the patient-near end of the guide rail, covers and largely or completely closes the guide rail or at least the guide channel on the upper face of the guide rail, and the intubation device has a second fixing device with which a position of the intubation device relative to a patient, in particular the angular position, can be fixed steplessly or in a plurality of fine steps.

14. An intubation device for intubating a patient with an endotracheal tube, comprising:

a) a handle for holding the intubation device, b) a guide rail connected to the handle, wherein the guide rail comprises a guide channel, wherein the guide rail extends in a longitudinal direction from a patient-remote end to a patient-near end, wherein the guide rail is configured for guiding the endotracheal tube, wherein the guide rail has an upper face configured for facing toward a patient's tongue during an intubation procedure, (c) an epiglottis lifter configured for lifting a patient's epiglottis, wherein the epiglottis lifter is mounted movably on a component of the intubation device via at least one bearing element, (d) at least one optical detection device in either or both a region of the patient-near end of the guide rail and/or on the epiglottis lifter in the region of the patient-near end of the guide rail, (e) wherein the epiglottis lifter, at least in the region of the patient-near end of the guide rail, covers and largely or completely closes the guide rail or at least the guide channel on the upper face of the guide rail, and wherein the epiglottis lifter at the region of the patient-remote end of the guide rail comprises a slit-shaped recess bounded on each side by a side web.

* * * * *